United States Patent
Misek et al.

(10) Patent No.: US 10,172,746 B2
(45) Date of Patent: Jan. 8, 2019

(54) DISPOSABLE ABSORBENT ARTICLES INCORPORATING BLACK-FREE COLORANTS

(71) Applicant: Kimberly-Clark Worldwide, Inc., Neenah, WI (US)

(72) Inventors: Jennifer L. Misek, Cumming, GA (US); Brian K. Rhodes, Winneconne, WI (US); Terri L. Meisel, Appleton, WI (US); Cole W. Poole, Appleton, WI (US); Shannon K. Melius, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 190 days.

(21) Appl. No.: 15/246,987

(22) Filed: Aug. 25, 2016

(65) Prior Publication Data

US 2016/0361207 A1    Dec. 15, 2016

Related U.S. Application Data

(62) Division of application No. 12/580,765, filed on Oct. 16, 2009, now Pat. No. 9,456,936.

(51) Int. Cl.
*A61F 13/84* (2006.01)
*A61F 13/15* (2006.01)
(Continued)

(52) U.S. Cl.
CPC .. *A61F 13/15772* (2013.01); *A61F 13/15764* (2013.01); *A61F 13/51496* (2013.01);
(Continued)

(58) Field of Classification Search
CPC ............... A61F 13/84; A61F 13/15772; A61F 13/51496; A61F 2013/15796;
(Continued)

(56) References Cited

U.S. PATENT DOCUMENTS 5,235,515 A    8/1993    Ungpiyakul et al.
5,286,543 A    2/1994    Unqpiyakul et al.
(Continued)

FOREIGN PATENT DOCUMENTS

CN          1989220 A      6/2007
EP        1 994 917 B1     6/2011
WO     WO 2008/110944 A1   9/2008

OTHER PUBLICATIONS

Carbon Black , "Pigments, Inorganic," "Black Pigments," Kirk-Othmer Encyclopedia of Chemical Technology Online, published Aug. 19, 2005, p. 30, accessed electronically at http://onlinelibrary.wiley.com/doi/10.1002/0471238961.0914151814152215.a01.pub2/pdf.

(Continued)

*Primary Examiner* — George R Koch

(57) ABSTRACT

A disposable absorbent article is presenting having multiple components and including an inspection region subject to inspection using infrared radiation, wherein the inspection region includes a junction of two components; and a printed graphic in the inspection region, wherein the ink used to print the graphic includes no carbon black colorant such that the printed graphic is substantially transparent to infrared radiation. In addition, a disposable absorbent article having multiple components includes a printed graphic in an inspection region subject to inspection using infrared radiation, the printed graphic including black ink having no carbon black colorant such that the printed graphic is substantially transparent to infrared radiation.

4 Claims, 5 Drawing Sheets

(51) Int. Cl.
 *A61F 13/514* (2006.01)
 *G01N 21/3554* (2014.01)

(52) U.S. Cl.
 CPC ......... *A61F 13/84* (2013.01); *G01N 21/3554* (2013.01); *A61F 2013/1578* (2013.01); *A61F 2013/15243* (2013.01); *A61F 2013/15788* (2013.01); *A61F 2013/15796* (2013.01); *A61F 2013/8497* (2013.01); *Y10T 428/2481* (2015.01); *Y10T 428/24802* (2015.01)

(58) Field of Classification Search
 CPC ... A61F 2013/15788; A61F 203/15243; Y10T 428/2481; Y10T 428/24802
 USPC .................. 156/64; 428/195.1, 196; 382/141
 See application file for complete search history.

(56) References Cited

U.S. PATENT DOCUMENTS

| | | |
|---|---|---|
| 6,174,400 B1 | 1/2001 | Krutak et al. |
| 6,224,699 B1 | 5/2001 | Bett et al. |
| 6,253,159 B1 | 6/2001 | Bett et al. |
| 6,352,497 B1 | 3/2002 | Hensley et al. |
| 6,354,984 B1 | 3/2002 | Hensley et al. |
| 6,408,917 B1 | 6/2002 | Bett et al. |
| 6,444,064 B1 | 9/2002 | Henry et al. |
| 6,565,686 B2 | 5/2003 | Bett et al. |
| 6,885,451 B2 | 4/2005 | Vogt et al. |
| 6,888,143 B2 | 5/2005 | Voqt et al. |
| 6,927,857 B2 | 8/2005 | Koele et al. |
| 7,537,585 B2 | 5/2009 | Christon et al. |
| 2003/0169433 A1 | 9/2003 | Koele et al. |
| 2003/0229325 A1 | 12/2003 | Belau et al. |
| 2005/0015066 A1 | 1/2005 | Anderson et al. |
| 2005/0122531 A1 | 6/2005 | Koele et al. |
| 2006/0021536 A1 | 2/2006 | Song et al. |
| 2006/0025736 A1 | 2/2006 | Berq et al. |

OTHER PUBLICATIONS

When Black is White, Paint and Coatings Industry, published Dec. 22, 2000, accessed electronically at "http://www.pcimag.com/articles/86552-when-black-is-white", pp. 1-10.

DISPOSABLE ABSORBENT ARTICLES INCORPORATING BLACK-FREE COLORANTS

RELATED APPLICATIONS

The present application is a divisional application, and claims priority to U.S. patent application Ser. No. 12/580,765, filed on Oct. 16, 2009, now U.S. Pat. No. 9,456,936, and the contents of which is incorporated herein by reference.

BACKGROUND

The present disclosure relates to detecting the presence, position, concentration and/or distribution of one or more components in a composite article, and to registration inspection of a composite article, using infrared radiation and infrared detectors in conjunction with the addition of inks transparent to infrared radiation.

A vast number of applications exist in which it is necessary or desirable to monitor the presence and/or position of one or more components of a composite article during manufacturing. For instance, in a largely automated process for manufacturing disposable absorbent products such as diapers and incontinence products, certain components (e.g., support layers, absorbent pads, elastic components, fastener components, etc.) must be positioned or aligned with respect to each other and/or other components in order to produce an acceptable product. Accordingly, inspection systems are commonly used to detect the positions of such components during manufacturing. If an inspection system determines that one or more components are out of position and thus do not properly register with other components, the inspection system typically outputs one or more signals indicating that certain articles should be culled and discarded, that the process should be adjusted so as to bring out-of-position components into proper position, that the process should be adjusted so that subsequent components are brought into proper registration with one another, etc.

Although highly useful for many applications, common inspection systems have certain shortcomings. For example, such systems are not well suited for determining the presence and/or positions of components underlying other components which are substantially opaque to visible and/or ultraviolet light. Additionally, such systems are not well suited to determining the presence and/or positions of components which tend to scatter visible and ultraviolet light.

Prior art inspection systems and processes are not well suited to detecting the distribution and/or concentration level (e.g., quantity) of certain product components. Certain substances including colorants added to increasingly complex and garment-like articles have the effect of inadvertently and unintentionally acting as infrared blockers, potentially disrupting the expected performance of the kinds of inspection systems described herein.

SUMMARY

To solve these and other needs in the art, the present disclosure illustrates processes and systems for detecting the presence, position, distribution and/or concentration of one or more components in a composite article, including adjacent components, overlapping components, and components which overlie or underlie other components, including components which are disposed or sandwiched between other components, without interference from infrared-radiation-absorbing inks. The present disclosure also relates to composite articles produced or inspected using such processes and systems. The disclosure is especially well suited to detecting properties of disposable absorbent articles undergoing fabrication and/or quality inspection, although the disclosure is far from so limited, as will be apparent from the description below.

A disposable absorbent article having multiple components includes an inspection region subject to inspection using infrared radiation, wherein the inspection region includes a junction of two components; and a printed graphic in the inspection region, wherein the ink used to print the graphic includes no carbon black colorant such that the printed graphic is substantially transparent to infrared radiation.

In addition, a disposable absorbent article having multiple components includes a printed graphic in an inspection region subject to inspection using infrared radiation, the printed graphic including black ink having no carbon black colorant such that the printed graphic is substantially transparent to infrared radiation.

Further, a disposable absorbent article having multiple components includes a printed graphic including ink having no carbon black colorant such that the printed graphic is substantially transparent to infrared radiation, wherein the printed graphic has a CIELab L* less than 80 and a CIELab C* greater than 1.5.

Also, a method for manufacturing a disposable absorbent article including a printed graphic includes printing an article component with ink free of carbon black, wherein the printed graphic has a CIELab L* less than 80 and a CIELab C* greater than 1.5; joining the article component to a second article at a junction to form the article, wherein the printing coincides with the junction; and passing the article through an infrared inspection station to inspect the junction without interference from the printing.

Additionally, a method for controlling the manufacture of a disposable absorbent article includes printing first and second components with an ink transparent to infrared radiation; aligning the printed first component with the printed second component; affixing the first component to the second component to form a junction; and passing the junction through an infrared inspection station to confirm the alignment of the first and second components.

In addition, a process for detecting whether one or more components are properly positioned in a composite article includes printing one or more components of the composite article with an ink transparent to infrared radiation; irradiating the composite article with infrared radiation;

and producing an image from the near infrared or infrared radiation received from the irradiated composite article. The process also includes identifying a position of a first variation in the produced image which represents an edge position of a first component in the composite article; and comparing the identified position with predetermined position data to thereby determine whether the first component is properly positioned in the composite article.

Finally, a component for use in a composite disposable absorbent garment includes a printed graphic overlying an edge of the component, wherein the printed graphic consists only of one or more inks transparent to infrared radiation to prevent the printed graphic from blocking infrared detection when the component is subjected to an infrared radiation-producing inspection system. Other features of the disclosure will be in part apparent and in part pointed out hereinafter.

Other objects and advantages of the present disclosure will become more apparent to those skilled in the art in view of the following description and the accompanying drawings.

BRIEF DESCRIPTION OF THE DRAWINGS

The present disclosure will be more fully understood, and further features will become apparent, when reference is made to the following detailed description and the accompanying drawings. The drawings are merely representative and are not intended to limit the scope of the claims.

Figure 1:
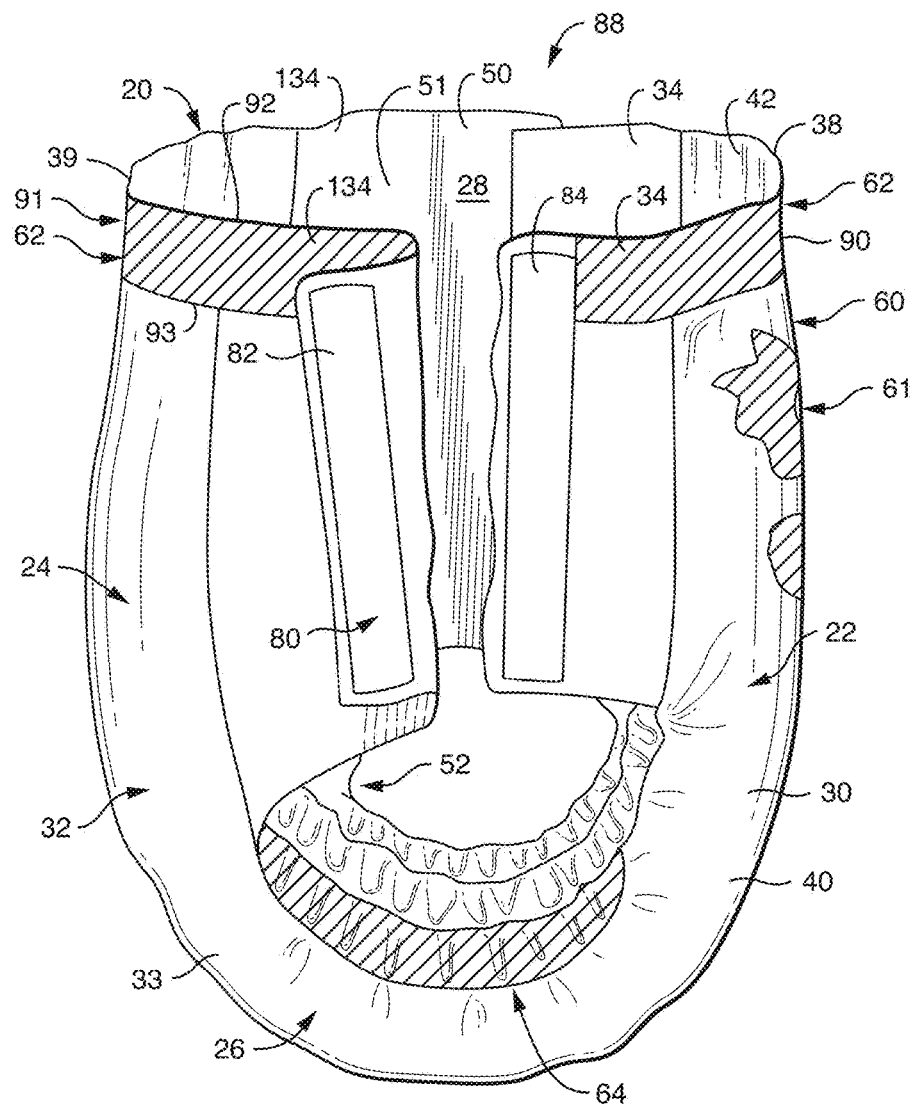
FIG. 1 is a side elevation of a child's training pants with a fastening system of the training pants shown connected on one side of the training pants and disconnected on the other side of the training pants.

Repeat use of reference characters in the present specification and drawings is intended to represent the same or analogous features or elements of the present disclosure. The drawings are representational and are not necessarily drawn to scale. Certain proportions thereof might be exaggerated, while others might be minimized.

DETAILED DESCRIPTION

It is to be understood by one of ordinary skill in the art that the present discussion is a description of exemplary aspects of the present disclosure only, and is not intended as limiting the broader aspects of the present disclosure.

The methods and apparatus of the present disclosure can be used to make a variety of pre-fastened articles such as disposable absorbent garments including diapers, training pants, feminine hygiene products, incontinence products, medical garments, other personal care or health care garments, swim pants, athletic clothing, pants and shorts, and the like. More particularly, the methods and apparatus of the present disclosure can be used to make articles in which at least two elements of the article are connected together during the making thereof to assemble or "pre-fasten" the article. For ease of explanation, the methods and apparatus of the present disclosure are hereafter described in connection with making pre-fastened child's pants, generally indicated as 20 in FIG. 1. In particular, the methods and apparatus will be described in terms of those for making pre-fastened disposable pants as described in U.S. patent application Ser. No. 09/444,083 titled "Absorbent Articles With Refastenable Side Seams" and filed Nov. 22, 1999 (corresponding to PCT application WO 00/37009 published Jun. 29, 2000) by A. L. Fletcher et al., the disclosure of which is incorporated herein by reference. Pants 20 can also be constructed using the methods and apparatus disclosed in U.S. Pat. No. 4,940,464 issued Jul. 10,1990 to Van Gompel et al.; and U.S. Pat. No. 5,766,389 issued Jun. 16, 1998 to Brandon et al.; the disclosures of which are also incorporated herein by reference.

It should be understood that as used herein, the term "component" includes not only discrete objects, but also objects yet to be formed into discrete objects (e.g., objects yet to be severed into discrete objects from a continuous sheet or web of material), particles (e.g., superabsorbent particles or polymers), adhesives, lotions, ointments, and other substances, as well as portions or characteristics of any such components including, for example, fold lines, bond lines (e.g., ultrasonic bond lines), bonded or adhered regions, and registration marks applied to or about components for subsequent detection during a manufacturing or inspection process. Further specific examples include side panels, outer covers, liners, adhesives, surge materials, elastic material, hook fastening devices, loop fastening devices, attachment tapes, tissue, films, conductive elements, and nonwoven materials.

With reference now to the drawings, and in particular to FIG. 1, a pair of pants 20 is illustrated in a partially fastened condition and include an absorbent chassis 32 having a front waist region 22, a back waist region 24, a crotch region 26 interconnecting the front and back waist regions, an inner surface 28 which is configured to contact the wearer, and an outer surface 30 opposite the inner surface and configured to contact the wearer's clothing. With additional reference to FIGS. 2 and 3, the absorbent chassis 32 also has a pair of laterally opposite side edges 36 and a pair of longitudinally opposite waist edges, respectively designated front waist edge 38 and back waist edge 39. The front waist region 22 is contiguous with the front waist edge 38, and the back waist region 24 is contiguous with the back waist edge 39.

Figure 2:
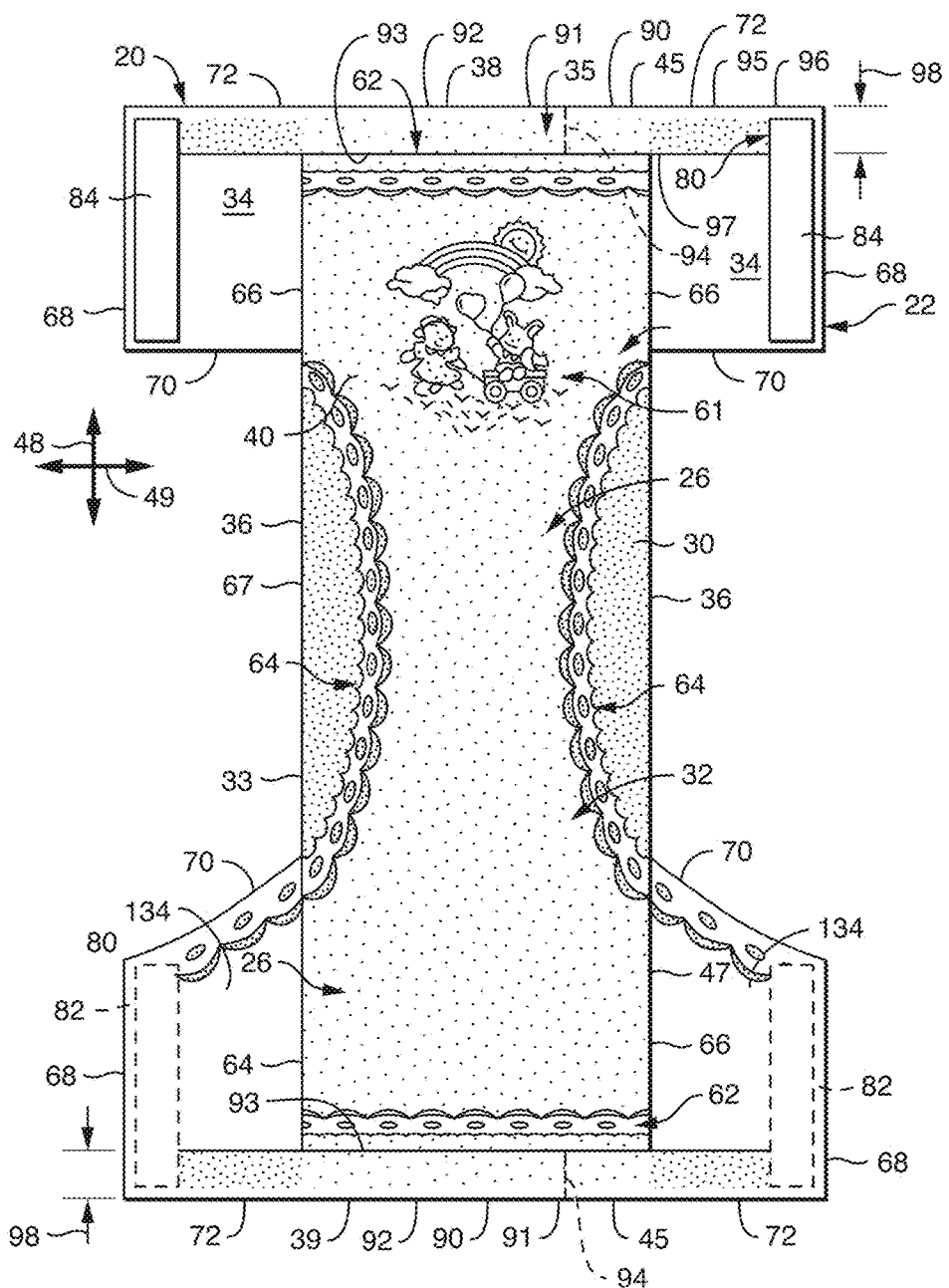
FIG. 2 is a bottom plan view of the training pants of FIG. 1 in an unfastened, stretched and laid flat condition to show the surface of the training pants which faces away from the wearer.

The illustrated absorbent chassis 32 includes a composite structure 33 (FIGS. 2 and 3), which when laid flat can be rectangular or any other desired shape, and has a pair of laterally opposite front side panels 34 and a pair of laterally opposite back side panels 134 extending outward therefrom. Each side panel 34, 134 includes a side panel central region 76 positioned generally on each side panel 34, 134, and does not include a waistband or leg bands (FIG. 2). The side panel central region 76 has a side panel central region appearance, which is the physical appearance of the side panel central region 76.

Figure 3:
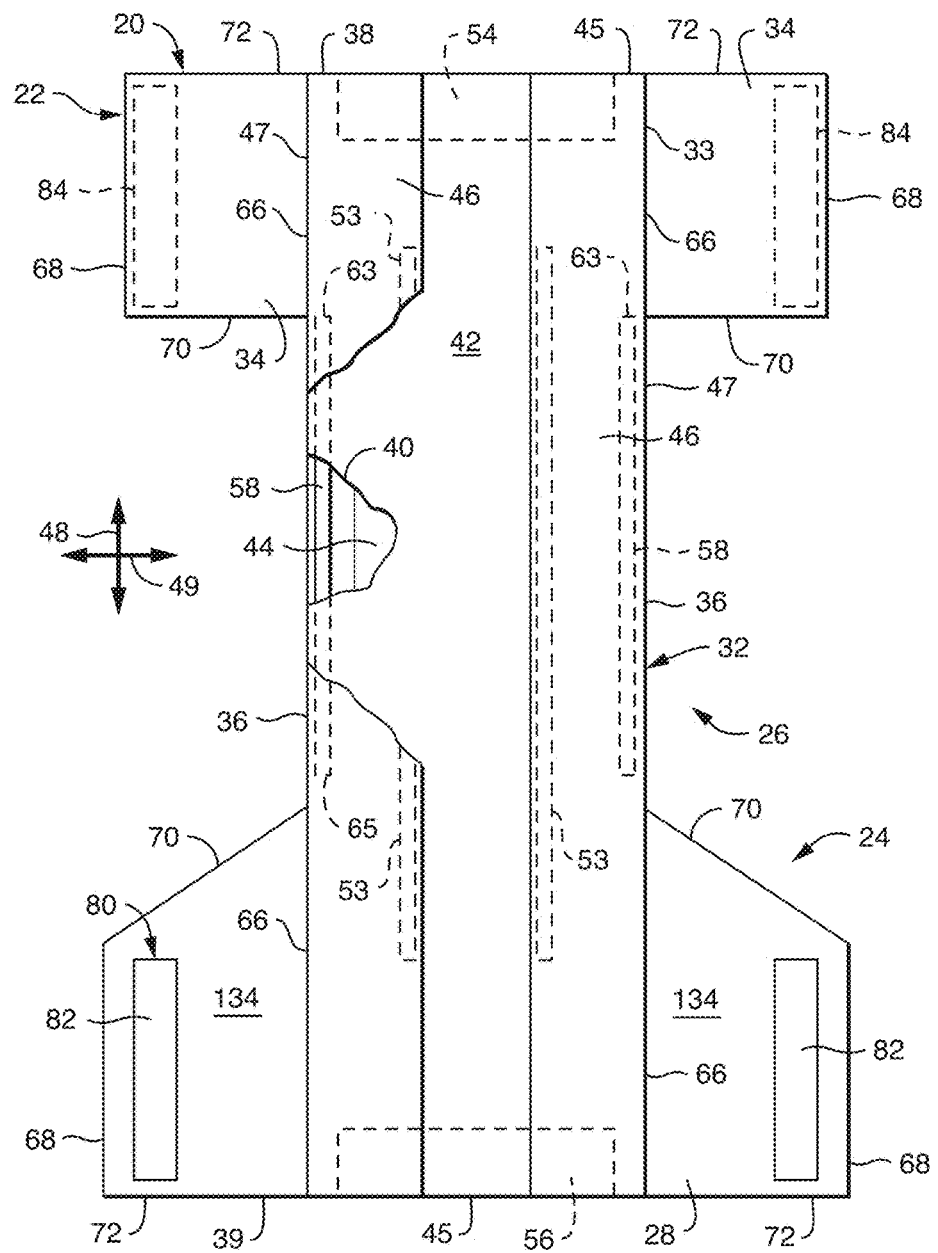
FIG. 3 is a top plan view of the training pants in its unfastened, stretched and laid flat condition to show the surface of the training pants which faces the wearer when the training pants are worn, with portions of the training pants being cut away to reveal underlying features.

The composite structure 33 and side panels 34, 134 can include two or more separate elements, as shown in FIG. 1, or be integrally formed. Integrally formed side panels 34, 134 and composite structure 33 would include at least some common materials, such as the bodyside liner, flap composite, outer cover, other materials and/or combinations thereof, and could define a one-piece elastic, stretchable, or non-stretchable pants. The illustrated composite structure 33 includes an outer cover 40, a bodyside liner 42 (FIGS. 1 and 3) connected to the outer cover in a superposed relation, an absorbent assembly 44 (FIG. 3) disposed between the outer cover and the bodyside liner, and a pair of containment flaps 46 (FIG. 3). The illustrated composite structure 33 has opposite ends 45 (FIGS. 2 and 3) that form portions of the front and back waist edges 38 and 39, and opposite side edges 47 which form portions of the side edges 36 of the absorbent chassis 32 (FIGS. 2 and 3). The outer cover 42 includes an outer cover central region 75 positioned generally in the front and/or back waist regions 22, 24, and does not include a waistband or leg bands (FIG. 2). The outer cover central region 75 has an outer cover central region appearance, which is the physical appearance of the outer cover central region 75.

For reference, arrows 48 and 49 (FIGS. 2 and 3) depict the orientation of the longitudinal axis and the transverse or lateral axis, respectively, of the pants 20.

With the pants 20 in the fastened position as partially illustrated in FIG. 1, the front and back side panels 34, 134 are connected together by a fastening system 80 to define a three-dimensional pants configuration having an interior space 51, a waist opening 50 for receiving the wearer into the interior space of the pants, a pair of leg openings 52 and engagement seams 88 along which the side panels 34, 134 are connected. The interior space 51 of the pants 20 is thus bounded by the absorbent chassis 32, the engagement seams 88 and the portions of the side panels 34, 134 extending on opposite sides of the engagement seams 88 (e.g., between the engagement seams 88 and the absorbent chassis 32). As used herein, the "interior space" 51 is intended to refer to the space between any two portions of a three-dimensional article which generally oppose each other. It is understood that a transverse cross-section of the article need not be closed, e.g., continuous, to define the interior space 51. For example, a two-dimensional article can be generally folded over on itself so that two portions of the article oppose each other to define an interior space of the article therebetween. Thus, the interior space 51 of the pants 20 shown in FIG. 1 can be defined by the side panels 34, 134 themselves or, if the side panels are fully straightened therebetween, the interior space is defined by a combination of the side panels and the front and back waist regions 22, 24 of the absorbent chassis 32.

The front waist region 22 includes the portion of the pants 20 which, when worn, is positioned on the front of the wearer while the back waist region 24 includes the portion of the pants which, when worn, is positioned on the back of the wearer. The crotch region 26 of the pants 20 includes the portion of the pants 20 which, when worn, is positioned between the legs of the wearer and covers the lower torso of the wearer. The front and back side panels 34 and 134 include the portions of the pants 20 which, when worn, are positioned on the hips of the wearer. The waist edges 38 and 39 of the absorbent chassis 32 are configured to encircle the waist of the wearer when worn and together define the waist opening 50 (FIG. 1). Portions of the side edges 36 in the crotch region 26 generally define the leg openings 52.

Figure 4:
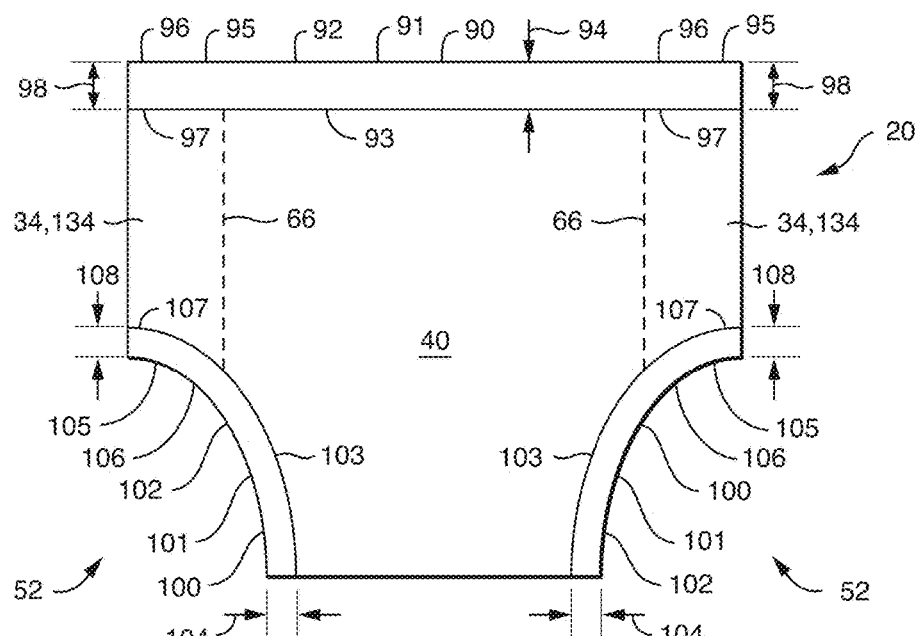
FIG. 4 is a schematic view of the pants of FIG. 1 showing a waistband and leg bands.

In another aspect of the present disclosure best illustrated in FIGS. 2 and 4, the pants 20 also include a printed waistband 90. The printed waistband 90 includes a waistband outer cover portion 91 disposed on the absorbent chassis 32 adjacent the waist opening 50. The waistband outer cover portion 91 includes a distal edge 92, a proximal edge 93, and a longitudinal height 94, which is the longitudinal distance between the proximal edge 93 and the distal edge 92. The printed waistband 90 also includes a waistband first side panel portion 95 disposed on one of the side panels 34, 134 adjacent the waist opening 50. The waistband first side panel portion 95 includes a distal edge 96, a proximal edge 97, and a longitudinal height 98, which is the longitudinal distance between the proximal edge 97 and the distal edge 96. In addition, each other article component adjacent the waist opening 50 can have a portion of the printed waistband 90 with similar features.

In another aspect of the present disclosure best illustrated in FIG. 4, the pants 20 also include a printed leg band 100. The printed leg band 100 includes a leg band outer cover portion 101 disposed on the absorbent chassis 32 adjacent the leg opening 52. The leg band outer cover portion 101 includes a distal edge 102, a proximal edge 103, and a longitudinal height 104, which is the longitudinal distance between the proximal edge 103 and the distal edge 102. The printed leg band 100 also includes a leg band first side panel portion 105 disposed on one of the side panels 34, 134 adjacent the leg opening 52. The leg band first side panel portion 105 includes a distal edge 106, a proximal edge 107, and a longitudinal height 108, which is the longitudinal distance between the proximal edge 107 and the distal edge 106. In addition, each other article component adjacent the leg opening 52 can have a portion of the printed leg band 100 with similar features. The pants 20 preferably includes a printed leg band 100 encircling each leg opening 52.

As used herein, the longitudinal height of a printed waistband 90 or of a printed leg band 100 is generally the distance between the distal and proximal edges of that band. Some bands, however, do not have linear edges. For example, bands can be scalloped, sinusoidal, arcuate, or of any other non-linear design. In such cases, the longitudinal height is the greatest distance between a distal edge and a proximal edge.

Additional detail with respect to alignment and misalignment of printed waistbands and leg bands can be found in U.S. patent application Ser. No. 12/580529, entitled "Alignment Of Leg And Waist Bands On Disposable Absorbent Articles," which is incorporated herein by reference to the extent it does not conflict herewith.

The absorbent chassis 32 is configured to contain and/or absorb any exudates discharged from the wearer. For example, the absorbent chassis 32 desirably, although not necessarily, includes the pair of containment flaps 46 which are configured to provide a barrier to the transverse flow of body exudates. A flap elastic member 53 (FIG. 3) can be operatively joined with each containment flap 46 in any suitable manner as is well known in the art. The elasticized containment flaps 46 define an unattached edge which assumes an upright configuration in at least the crotch region 26 of the pants 20 to form a seal against the wearer's body. The containment flaps 46 can be located along the side edges 36 of the absorbent chassis 32, and can extend longitudinally along the entire length of the absorbent chassis 32, or can only extend partially along the length of the absorbent chassis 32. Suitable constructions and arrangements for the containment flaps 46 are generally well known to those skilled in the art and are described in U.S. Pat. No. 4,704,116 issued Nov. 3, 1987 to Enloe, which is incorporated herein by reference.

To further enhance containment and/or absorption of body exudates, the pants 20 desirably, although not necessarily, include a front waist elastic member 54, a rear waist elastic member 56, and leg elastic members 58, as are known to those skilled in the art (FIG. 3). The waist elastic members 54 and 56 can be operatively joined to the outer cover 40 and/or the bodyside liner 42 along the opposite waist edges 38 and 39, and can extend over part or all of the waist edges. The leg elastic members 58 can be operatively joined to the outer cover 40 and/or the bodyside liner 42 along the opposite side edges 36 and positioned in the crotch region 26 of the pants 20. The leg elastic members 58 can be longitudinally aligned along each side edge 47 of the composite structure 33. Each leg elastic member 58 has a front terminal point 63 and a back terminal point 65, which represent the longitudinal ends of the elastic gathering caused by the leg elastic members. The front terminal points 63 can be located adjacent the longitudinally innermost parts of the front side panels 34, and the back terminal points 65 can be located adjacent the longitudinally innermost parts of the back side panels 134.

As shown in FIGS. 1 and 2, the pants 20 and in particular the outer cover 40 desirably includes one or more appearance-related components. Examples of appearance-related components include, but are not limited to, graphics; highlighting or emphasizing leg and waist openings in order to make product shaping more evident or visible to the user; highlighting or emphasizing areas of the product to simulate functional components such as elastic leg bands, elastic waistbands, simulated "fly openings" for boys, ruffles for girls; highlighting areas of the product to change the appearance of the size of the product; registering wetness indicators, temperature indicators, and the like in the product; registering a back label, or a front label, in the product; and registering written instructions at a desired location in the product.

The illustrated pair of pants 20 is designed for use by young girls and includes a registered outer cover graphic 60 (FIGS. 1 and 2). In this design, the registered graphic 60 includes a primary pictorial image 61, simulated waist ruffles 62, and simulated leg ruffles 64. The primary pictorial image 61 includes an object graphic such as a rainbow, sun, clouds, animal characters, wagon and balloons. Any suitable design can be utilized for pants intended for use by young girls, so as to be aesthetically and/or functionally pleasing to them and the caregiver. The appearance-related components are desirably positioned on the pants 20 at selected locations, which can be carried out using the methods disclosed in U.S. Pat. No. 5,766,389 issued Jun. 16, 1998 to Brandon et al., the entire disclosure of which is incorporated herein by reference. The primary pictorial image 61 is desirably positioned in the front waist region 22 along the longitudinal center line of the pants 20.

The printed graphics on the pants 20 can share a color palette, can be of the same color, can be of complementary colors, or can follow any suitable color scheme. Different areas of the pants 20 can also be printed with similar or identical graphical elements such as stars, circles, butterflies, etc. Different areas of the pants 20 can also be printed with similar or identical graphics that share a graphic theme. For example, the pants 20 can be printed with flowers that might or might not be identical in size, type, color, etc., but that all share the flower theme. In another aspect, the article can be reverse printed such that graphical elements, for example, appear as an absence of printing.

As noted previously, the illustrated pants 20 have front and back side panels 34 and 134 disposed on each side of the absorbent chassis 32. The front side panels 34 can be permanently bonded along seams 66 to the composite structure 33 of the absorbent chassis 32 in the respective front and back waist regions 22 and 24. More particularly, as seen best in FIGS. 2 and 3, the front side panels 34 can be permanently bonded to and extend transversely outward beyond the side edges 47 of the composite structure 33 in the front waist region 22, and the back side panels 134 can be permanently bonded to and extend transversely outward beyond the side edges of the composite structure in the back waist region 24. The side panels 34 and 134 can be bonded to the composite structure 33 using attachment means known to those skilled in the art such as adhesive, thermal, or ultrasonic bonding. Alternatively, the side panels 34 and 134 can be formed as an integral portion of a component of the composite structure 33. For example, the side panels can include a generally wider portion of the outer cover 40, the bodyside liner 42, and/or another component of the absorbent chassis 32. The front and back side panels 34 and 134 can be permanently bonded together or be releasably connected with one another such as by the fastening system 80 of the illustrated aspect.

As best illustrated in FIGS. 2 and 3, the front and back side panels 34, 134 each have an outer edge 68 spaced laterally from the seam 66, a leg end edge 70 disposed toward the longitudinal center of the pants 20, and a waist end edge 72 disposed toward a longitudinal end of the pants. The leg end edge 70 and waist end edge 72 extend from the side edges 47 of the composite structure 33 to the outer edges 68. The leg end edges 70 of the side panels 34 and 134 form part of the side edges 36 of the absorbent chassis 32. In the back waist region 24, the leg end edges 70 are desirably, although not necessarily, curved and/or angled relative to the transverse axis 49 to provide greater coverage toward the back of the pants 20 as compared to the front of the pants 20. The waist end edges 72 are desirably parallel to the transverse axis 49. The waist end edges 72 of the front side panels 34 form part of the front waist edge 38 of the absorbent chassis 32, and the waist end edges 72 of the back side panels 134 form part of the back waist edge 39 of the absorbent chassis. The waist end edges 72 are generally aligned or co-linear with the front and back waist edges 38, 39.

In particular aspects for improved fit and appearance, the side panels 34, 134 desirably have an average length measured parallel to the longitudinal axis 48 which is about 15 percent or greater, and particularly about 25 percent or greater, of the overall length of the pants, also measured parallel to the longitudinal axis 48. For example, in pants 20 having an overall length of about 54 centimeters, the side panels 34, 134 desirably have an average length of about 10 centimeters or greater, such as about 15 centimeters. While each of the side panels 34, 134 extends from the waist opening 50 to one of the leg openings 52, the illustrated back side panels 134 have a continually decreasing length dimension moving from the seam 66 to the outer edge 68, as is best shown in FIGS. 2 and 3.

Each of the side panels 34, 134 can include one or more individual, distinct pieces of material. In particular aspects, for example, each side panel 34, 134 can include first and second side panel portions that are joined at a seam, or can include a single piece of material which is folded over upon itself (not shown).

The side panels 34, 134 desirably, although not necessarily, include an elastic material capable of stretching in a direction generally parallel to the transverse axis 49 of the pants 20. Suitable elastic materials, as well as one process of incorporating elastic side panels into pants, are described in the following U.S. Pat. No. 4,940,464 issued Jul. 10, 1990 to Van Gompel et al.; U.S. Pat. No. 5,224,405 issued Jul. 6, 1993 to Pohjola; U.S. Pat. No. 5,104,116 issued Apr. 14, 1992 to Pohjola; and U.S. Pat. No. 5,046,272 issued Sep. 10, 1991 to Vogt et al.; all of which are incorporated herein by reference. An alternative elastic material is described below. In particular aspects, the elastic material includes a stretch-thermal laminate (STL), a neck-bonded laminate (NBL), a reversibly necked laminate, or a stretch-bonded laminate (SBL) material. Methods of making such materials are well known to those skilled in the art and described in U.S. Pat. No. 4,663,220 issued May 5, 1987 to Wisneski et al.; U.S. Pat. No. 5,226,992 issued Jul. 13, 1993 to Morman; and European Patent Application No. EP 0 217 032 published on Apr. 8, 1987 in the names of Taylor et al.; all of which are incorporated herein by reference. Alternatively, the side panel material can include other woven or nonwoven materials, such as those described above as being suitable for the outer cover 40 or bodyside liner 42; mechanically prestrained composites; or stretchable but inelastic materials.

Further detail with respect to elastic laminates of the present disclosure can be found in co-pending U.S. Patent Publication No. 2008/0095978 entitled "Nonwoven Composite Containing An Apertured Elastic Film," which is incorporated herein by reference to the extent it does not conflict herewith.

Pants 20 can have the side panels 34, 134 affixed to each other for securing the pants 20 about the waist of the wearer. The side panels 34, 134 can be affixed by bonding, mechanical fasteners, or any other suitable method, and can be affixed permanently, in a tearable manner, or in a refastenable manner. The illustrated pants 20 includes the fastening system 80 for refastenably securing the pants about the waist of the wearer. The illustrated fastening system 80 includes first fastening components 82 adapted for refastenable engagement to corresponding second fastening components 84. In one aspect, one surface of each of the first fastening components 82, 84 includes a plurality of engaging elements which project from that surface. The engaging elements of the first fastening components 82 are adapted to repeatedly engage and disengage engaging elements of the second fastening components 84.

The fastening components 82, 84 can comprise separate elements bonded to the side panels 134, 34, or they may be integrally formed with the side panels. Thus, unless otherwise specified, the term "fastening component" includes separate components which function as fasteners, and regions of materials such as the side panels 34, 134 which function as fasteners. Moreover, a single material can define multiple fastening components to the extent that different regions of the material function as separate fasteners. The fastening components 82, 84 can be located on the side panels 134, 34, between the side panels such as on the absorbent chassis, or a combination of the two.

As described above, waist and leg openings of disposable absorbent articles are often created by joining multiple components. The present disclosure applies in particular to articles for which the circumference of either the waist or leg opening has more than two interfaces or junctions at which components are attached, bonded, etc., as is described in more detail above. The article can include one or more printed band features in the form of a waistband partially or completely encircling the waist opening and/or a leg band partially or completely encircling one or each leg opening. For example, a fully encircling waistband is achieved by attaching a pair of right and left side panels to each of the front and rear waist regions of an article's outercover and then bonding the front and back assemblies together at the sides to create a closed garment. In this example, the waistband encompasses six components (with the outer cover counting twice with its front and rear waist regions) and six junctions. Aligning each of these components properly is a complex process that is further complicated if printing on some or all components also needs to be aligned. In other aspects, a functional waistband that does or does not span the entire waist circumference can be attached to the outercover and/or side panels with similar complexity. The printed band feature can be of uniform or any other suitable appearance. Multiple printed band features, such as a waistband including a plurality of generally horizontal and adjoining lines, are considered to be a single band feature.

Similarly, a fully encircling leg band is also achieved by attaching a pair of right and left side panels to each of the front and rear waist regions of an article's outercover and then bonding the front and back assemblies together at the sides to create a closed garment. In this example, each leg band encompasses three components and three junctions. Aligning each of these components properly is a complex process that is further complicated if printing on some or all components also needs to be aligned. In other aspects, functional leg bands and leg elastics that do not span the entire leg circumference can be attached to the outercover and/or side panels.

Printing fully-encircling waist and leg bands provides a visual cue to a consumer of a fully-encircling functional waistband, which is a key component in giving the article an appearance of conventional underwear. Printing is leveraged to create the visual perception of a continuous waist and/or leg band material that exists across multiple pieces (e.g., side panels, outercover, waist elastics, and leg elastics). The printing can be applied to the garment or outward facing surfaces of the outer cover and side panels, the body or inward facing surfaces of the outercover and side panels, and/or sandwiched within material layers.

In an alternative aspect of the present disclosure, a waistband and/or a leg band is not required to have a distinct or abrupt edge. A gradation in the printing, such as a gradation from darker to lighter, can be employed for visual effect and, in some cases, to minimize the appearance of a misalignment offset. The same acceptable/unacceptable offset limits and features described herein can be applied to such a gradation with respect to its edges and/or longitudinal height.

The components can be printed prior to, during, or after the multiple components are combined to form the absorbent article. The printed waist/leg bands are substantially but not necessarily completely aligned at the seams (e.g., outercover to side panel, front to back side seams) and substantially encircle the waist and leg openings. The article can have additional printing or pigmentation to further enhance a more uniform, garment-like look.

In particular embodiments, after the first side panel is joined to the chassis to impart a pant-like configuration to the pants 20, the outer cover portion is in complete alignment with the first side panel portion. As used herein, "complete alignment" and variations thereof mean that the longitudinal height of the outer cover portion is the same as the longitudinal height of the first side panel portion, and further that the outer cover portion and the first side panel portion have no longitudinal offset from each other in the assembled pant-like configuration.

In other embodiments, after the first side panel is joined to the chassis to impart a pant-like configuration to the pants 20, the outer cover portion is in substantial alignment with the first side panel portion. As used herein, "substantial alignment" and variations thereof mean either that the longitudinal height of the outer cover portion is not the same as the longitudinal height of the first side panel portion, or that the outer cover portion and the first side panel portion are longitudinally offset from each other in the assembled pant-like configuration by the amounts described below.

U.S. Pat. No. 6,885,451 B2 to Vogt et al., incorporated herein by reference, illustrates a process of inspecting a composite article, such as an article having first and second panels in at least partially opposed, overlapping engagement with each other to determine whether the panels of the article are present and/or properly positioned. The process includes irradiating the composite article with radiation and producing an image from radiation received from the irradiated composite article. For example, when inspecting the composite article having side panels and a fastener, the overlapping engagement of the panels would be irradiated and the image from radiation received from the radiated panels and a fastener therebetween would be produced. The process further includes identifying the presence and/or position of one or more components in the produced image of the composite article. In one aspect, an underlying edge as described herein would be identified. The identified presence and/or position of the component(s) in the produced image is compared with reference data to thereby determine whether the component(s) of the composite article is present and/or properly positioned therein.

In one aspect of the present disclosure, infrared radiation is used to irradiate the overlapping engagement. By using infrared radiation rather than (or in addition to) visible light, the process can not only detect the presence and/or position of components which tend to scatter visible and ultraviolet light, including components which overlie other components, but also the presence and/or position of components which underlie other components, including components disposed or sandwiched between components which are substantially opaque to visible and ultraviolet light.

One exemplary system for implementing such a process is illustrated in U.S. Pat. No. 6,885,451 as referenced above. For example, the system can be used to inspect composite articles having first and second panels in at least partially opposed, overlapping engagement with each other and having an underlying edge for determining whether the panels of the article are present and properly positioned. The system includes a radiation source, such as an infrared source, for irradiating a composite article with infrared radiation. For example, the source can irradiate the overlapping engagement of the panels of the article noted above. The system further includes an infrared image capturing device such as a camera for producing, in this example, a two dimensional image from radiation transmitted through the composite article and received from the irradiated panels. The camera is operatively connected to a controller with an image analyzer, which itself is operatively connected to the camera for identifying in the image a presence and/or position of a component, such as a position of an edge, and for comparing the identified presence and/or position with predetermined (reference) data to thereby determine whether the edge is properly positioned in the composite article. Further detail is provided in U.S. Pat. No. 6,885,451 as referenced above To the extent that such components do not inherently provide an infrared response which readily permits their detection using incident infrared (or other) radiation and infrared detectors, such components can be provided with a suitable infrared marker so as to impart them with a desired response, such as is described in U.S. Pat. No. 6,927,857 to Koele et al., which is incorporated herein by reference.

While suited for a wide variety of applications, the present disclosure is particularly useful in the production of absorbent articles, such as disposable diapers, training pants, incontinence devices, sanitary napkins, and the like.

It should be apparent that the system is capable of detecting presence and positions of not only stacked components, but also overlapping components as well as non-overlapping adjacent components.

As used herein, "infrared radiation source" refers to any device capable of emitting radiation in the infrared spectrum (i.e., radiation having a wavelength between about 700 nanometers and one millimeter), regardless of whether it also emits radiation in other spectrums. Some examples of infrared radiation sources suitable for certain aspects of the present disclosure include infrared LEDs, mercury vapor lamps, argon lamps, arc lamps, lasers, etc. In contrast, "radiation source" refers to any device capable of emitting radiation in any spectrum, which may or may not include the infrared spectrum.

"Infrared detector" refers to any device having one or more sensor elements (including a matrix of sensor elements) capable of sensing infrared radiation, regardless of whether such device can also sense radiation in other spectrums. Thus, included in this definition are existing vision inspection cameras which are capable of detecting not only visible and ultraviolet light, but also infrared radiation of wavelengths up to about 1200 nanometers (as noted above), line scan cameras capable of building an image one line at a time from infrared radiation received from an article as the article is moved relative thereto, as well as any other device capable of producing a one, two or three dimensional image from received infrared radiation including, without limitation, a charge coupled device ("CCD").

As alluded to above, any infrared detector used in the present disclosure (as well as any composite article to be detected thereby) can be provided with a filter for filtering unwanted wavelengths, including those in the infrared and/or other spectrums, as desired. Such filters include low-pass filters which remove radiation above a predefined wavelength, high-pass filters which remove radiation below a predefined wavelength, band-pass filters which remove all radiation except that having a wavelength within a predefined range, and combinations thereof. One or more of these filters can be useful for removing ambient, scattered, or even incident radiation (such as when detecting components which fluoresce at different wavelengths than the incident radiation) in any given application of the disclosure.

The infrared and other radiation sources described herein, as well as the infrared detectors, can include fiber optic devices in various applications of the disclosure, such as to precisely irradiate or detect radiation from a specific component or region in a composite article.

Figure 5:
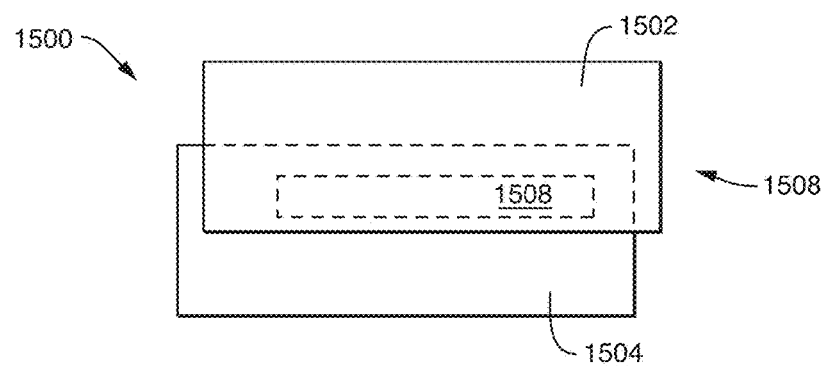
FIG. 5 is a top view of an exemplary disposable article having an inspection region of overlapping outer cover and side panel components.

In particular, FIG. 5 illustrates an inspection region 1508 of an article 1500 wherein one end portion of a first side panel 1502 of the article 1500 is joined with one end portion of an outer cover 1504 via a bonding region 1506 (shown in phantom), with the first side panel 1502 overlapping the outer cover 1504 and the bonding region 1506. The inspection region 1508 can be taken as the entire area shown in FIG. 5, or can be limited to an area of interest such as the vicinity of the bonding region 1506. Any printed graphics applied particularly to the side panel portion 1502 or to the outer cover portion 1504 in this inspection region 1508 will need to be free of carbon black colorant if this inspection region 1508 is to be subject to inspection using infrared radiation.

Figures 6A, 6B:
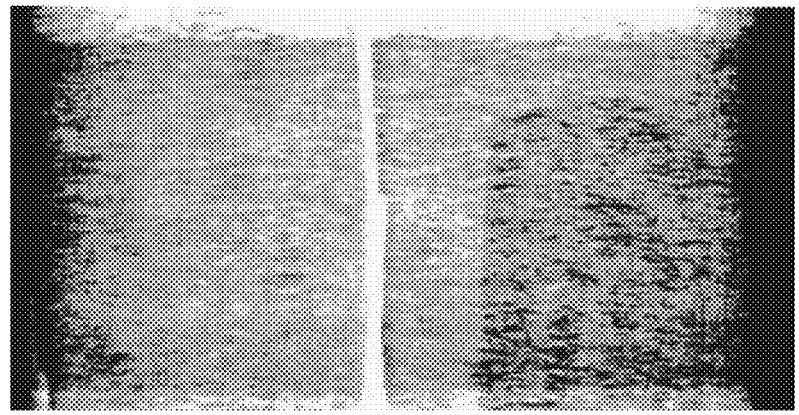
FIGS. 6(a), 6(b), 7(a), and 7(b) are photographs showing printed graphics using identical colors formulated without (6(a) and 7(a)) and with (6(b) and 7(b)) carbon black colorant.
Figures 7A, 7B:
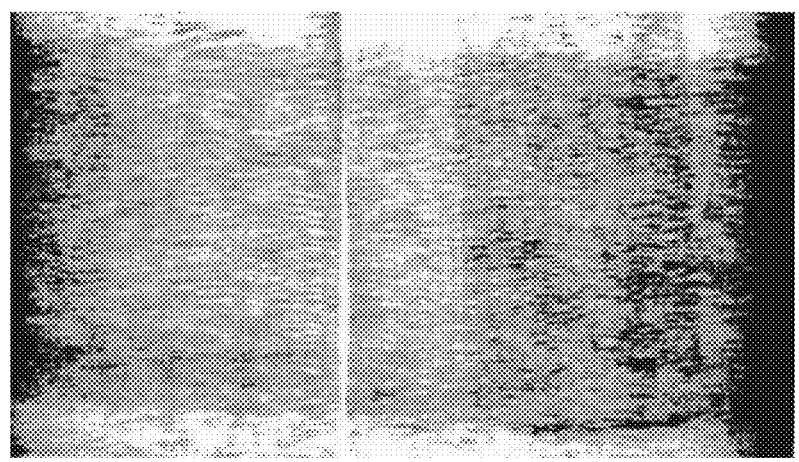

Further, FIGS. 6(a)-7(b) illustrate the effects of carbon black colorant in an ink used to print a printed graphic. FIGS. 6(a) and 6(b) illustrate a nonwoven material printed with two different formulations of Pantone 5767U. The ink in FIG. 6(a) was formulated without carbon black colorant, whereas the ink in FIG. 6(b) was conventionally formulated with carbon black colorant. Similarly, FIGS. 7(a) and 7(b) illustrate a nonwoven material printed with two different formulations of Pantone 289U. The ink in FIG. 7(a) was formulated without carbon black colorant, whereas the ink in FIG. 7(b) was conventionally formulated with carbon black colorant. All samples were then subject to a test infrared inspection system as described below. It is apparent that there is a significant difference in the resulting images. The printed graphics including carbon black colorant are quite visible, whereas the printed graphics with no carbon black colorant are essentially transparent.

In accordance with one aspect of the infrared detection system for the inspection of composite articles described herein, the degree to which one or more components of the composite article absorbs or reflects infrared radiation, and hence the degree to which the component can be detected by the infrared system, can be significantly but undesirably increased by printing in an inspection region or region of interest using conventional inks. The inspection region is an arbitrary area selected as an area of interest to the inspection process. The inspection region is typically a junction of two components that needs to be inspected using infrared radiation, but the inspection region can be anywhere on an article including one in which a hidden component needs to be detected, or one in which the intentional or unintentional absence of a component needs to be confirmed.

Increasing the garment-like appearance of a disposable absorbent article can include printing across much or the entire outer surface of the article, including printing on the outer cover, side panels, waistbands, leg bands, and any other structural feature. Conventional inks, however, can act as infrared blockers due, at least in part, to the presence of carbon black as a black colorant in many inks. Infrared blockers have the capacity to absorb (absorbing infrared blockers) or reflect (reflecting infrared blockers) infrared light. The introduction of such infrared blockers can significantly increase the absorbence or reflectance of components in the region of interest in the composite product resulting in an image other than that which is desired, and can undermine the detection and pinpointing of the cross direction and/or machine direction position of one or more components of the composite article.

It should be noted that inks including carbon black colorants can be used in any area of an article outside an inspection region. The limitation of avoiding carbon black colorant applies where such colorant could interfere with inspection.

It should also be noted that infrared blockers can be intentionally included to accentuate or intentionally block certain components. Such intentional inclusion of infrared blockers is described in greater detail in U.S. Pat. No. 6,927,857 to Koele et al. as referenced above.

More specifically, certain substances added to increasingly complex and garment-like articles have the effect of inadvertently and unintentionally acting as infrared blockers, potentially disrupting the expected performance of the kinds of inspection systems described herein. For example, improvements in article manufacture include increasingly sophisticated printing schemes, allowing such articles to more closely emulate garments and other wearable articles. Many of the colorants used in this printing, particularly darker colors, are formulated to include carbon black as a black colorant. It has been found that the carbon black in such colorants is an infrared blocker that can disrupt inspection system performance in the regions in which such ink is applied. In one example, a waistband is printed on a training pant along the waist edge of its chassis and across its side panels before these components are joined. Once joined to form a seam, that seam is inspected using an infrared inspection system to ensure proper alignment and attachment of the components. The printing on each component, however, can block the transmission of infrared radiation through the components, thus blocking the seam from proper inspection.

In one example, a disposable absorbent article printed with colorant including carbon black was inspected using an infrared inspection system. The inspection system detected primarily an expanse of black due to the colorant in the article's printed waistband and the colorant in the product graphics. The print as detected by the inspection system was dark enough to obscure contrasting shadows generated by the side seam bond pattern and the waist and leg machine direction offset, which are used to inform the vision system on whether to cull, adjust, etc.

Although eliminating the use of colorants in regions needing inspection is an option, the desire for advanced articles requires the use of colorants in any and all regions of such articles. As a result, colorants that are invisible or transparent to infrared radiation are needed for use in such articles. Colorants that conventionally include carbon black as a colorant were reformulated to match the original color without using carbon black. Such colorants can be described by industry standards, as described below.

The color of each colorant is described according to the Commission Internationale de l'Eclairage L*a*b* color space (hereinafter "CIELab"). CIELab is a mathematical tristimulus color scale based on the CIE 1976 standard. CIELab allows colors to be described quantitatively and with precision. CIELab allows a color to be plotted in three-dimensional space analogous to Cartesian xyz space. CIELab positions colors from green to red on what is traditionally the x-axis in Cartesian xyz space. CIELab identifies this axis as the a*-axis. A negative a* value represents green and a positive a* value represents red. CIELab positions colors from blue to yellow on what is traditionally the y-axis in Cartesian xyz space. CIELab identifies this axis as the b*-axis. Negative b* values represent blue and positive b* values represent yellow. For its third dimension, CIELab positions lightness on what is traditionally the z-axis in Cartesian xyz space. CIELab identifies this axis as the L*-axis. The L*-axis ranges in value from 100, which is white, to 0, which is black. An L* value of 50 represents a mid-tone gray (provided a* and b* are 0). Any color may be plotted in CIELab according to the three values (L*, a*, b*).

The three-dimensional CIELab allows the three color components of chroma, hue, and lightness to be calculated. The components of hue and chroma can be determined within the two-dimensional plane formed by the a*-axis and b*-axis. Chroma is the relative saturation of the perceived color and is determined by the distance from the origin as measured in the a*b* plane. Chroma for a particular (a*, b*) point is calculated according to the following formula: $C^* = \text{square root of } (a^{*2} + b^{*2})$. For example, a color with (a*, b*) values of (10, 0) would exhibit a lesser chroma than a color with (a*, b*) values of (20, 0). The latter color would qualitatively be perceived as being more red than the former color.

Hue is the relative red, yellow, green, and blue in a particular color. A ray can be created from the origin to any color point within the two-dimensional a*b* plane. Hue is the azimuthal angle measured from 0° (the positive a*-axis) to the created ray. As a result, hue can be any value of between 0° to 360°. Lightness is determined from the L* value with higher values being more white and lower values being more black.

Test Method And Examples

Inks that conventionally include carbon black as a colorant were reformulated to match the original color without using carbon black. Inks with and without black colorant were tested as follows. Testing was performed to evaluate the color values of the various inks using a BYK-Gardner Color-Guide Sphere set to the d65/10 for a fluorescent illuminant reading L*a*b* color values. After calibrating the instrument, samples of nonwovens such as VFL and the elastic laminate of the present disclosure with different ink formulations were placed on top of the white backing tile, which is placed on a horizontal surface. The white backing tile comes standard with the equipment: (Color reflectance) 90 by 90 mm, Avian Technologies part number ATROG-Cstm-95. The instrument is placed on the sample and held level to the tile. Three readings each of L*, a*, and b* were taken per sample and averaged. L*, a*, b*, and C* (calculated from a* and b*) are shown in the following tables.

Drawdowns of inks formulated by Sun with and without black colorant were made on VFL side panel material. The results are listed in Table 1.

TABLE 1

| Color | with black colorant | | | | without black colorant | | | |
|---|---|---|---|---|---|---|---|---|
| Name | L* | a* | b* | C* | L* | a* | b* | C* |
| Pantone 7483U | 72.68 | −8.83 | 6.41 | 10.9 | 70.40 | −7.26 | 4.90 | 8.8 |
| Pantone 5767U | 65.88 | −3.58 | 9.84 | 10.5 | 71.71 | −5.18 | 9.83 | 11.1 |
| Pantone 7459U | 67.43 | −7.28 | −11.09 | 13.3 | 70.35 | −8.14 | −10.89 | 13.6 |
| Pantone 255U | 67.97 | 9.00 | −6.46 | 11.1 | 58.71 | 13.97 | −10.52 | 17.5 |
| Pantone 716U | 75.12 | 12.81 | 18.23 | 22.3 | 76.66 | 13.23 | 19.15 | 23.3 |
| Pantone 289U | 61.58 | 1.37 | −10.87 | 11.0 | 61.27 | 1.73 | −10.42 | 10.6 |

Drawdowns on VFL side panel material were also made using two black ink formulations. Standard black is a standard black ink with carbon black as a black colorant, and trichromatic black is an ink that resembles black ink and that is formulated by combining other inks and includes no black colorant, and alternative black is a black ink formulated without the use of carbon black. The results are listed in Table 2.

TABLE 2

| Color | L* | a* | b* | C* |
|---|---|---|---|---|
| standard black | 68.12 | −0.17 | 1.36 | 1.4 |
| trichromatic black | 68.77 | 2.04 | −7.41 | 7.7 |

A different formulation of Pantone 289U without black colorant by Bemis was flexographically printed onto VFL side panel material. The results are listed in Table 3. The C* values are lower due in part to the amount of ink used in flexographic printing versus drawdown.

TABLE 3

| Color | L* | a* | b* | C* |
|---|---|---|---|---|
| Pantone 289U | 72.42 | −1.22 | −2.98 | 3.2 |

Any printing technique can be employed to apply an ink to the pleated surface of the meltblown facing, such as gravure printing, flexographic printing, screen printing, ink-jet printing, laser printing, thermal ribbon printing, piston printing, etc. In one particular aspect, ink-jet printing techniques are employed to apply an ink to the meltblown facing. Ink-jet printing is a non-contact printing technique that involves forcing an ink through a tiny nozzle (or a series of nozzles) to form droplets that are directed toward the support. Two techniques are generally utilized, i.e., "DOD" (Drop-On-Demand) or "continuous" ink-jet printing. In continuous systems, ink is emitted in a continuous stream under pressure through at least one orifice or nozzle. The stream is perturbed by a pressurization actuator to break the stream into droplets at a fixed distance from the orifice. DOD systems, on the other hand, use a pressurization actuator at each orifice to break the ink into droplets. The pressurization actuator in each system can be a piezoelectric crystal, an acoustic device, a thermal device, etc. The selection of the type of ink jet system varies on the type of material to be printed from the print head. For example, conductive materials are sometimes required for continuous systems because the droplets are deflected electrostatically.

The particular type or style of ink pattern is not a limiting factor of the disclosure, and can include, for example, any arrangement of stripes, bands, dots, or other geometric shape. The pattern can include indicia (e.g., trademarks, text, and logos), floral designs, abstract designs, any configuration of artwork, etc. The pattern can be targeted for a specific class of consumers. For example, in the case of diapers or training pants, the pattern can be in the form of cartoon characters, and so forth. It should be appreciated that the "pattern" can take on virtually any desired appearance.

The ink generally includes one or more colorants (e.g., pigments, dyes, etc.) that impart a certain color to the facing, such as black, white, yellow, cyan, magenta, red, green, blue, etc. For example, the colorant can be an inorganic and/or organic pigment. Some examples of commercially-available organic pigments that can be used in the present disclosure include those that are available from Clariant Corp. of Charlotte, N.C., under the trade designations GRAPHTOL® or CARTAREN®. Other pigments, such as lake compounds (blue lake, red lake, yellow lake, etc.), can also be employed. Inorganic and/or organic dyes can also be utilized as a colorant. Exemplary organic dye classes include triarylmethyl dyes, monoazo dyes, thiazine dyes, oxazine dyes, naphthalimide dyes, azine dyes, cyanine dyes, indigo dyes, coumarin dyes, benzimidazole dyes, paraquinoidal dyes, fluorescein dyes, diazonium salt dyes, azoic diazo dyes, phenylenediamine dyes, diazo dyes, anthraquinone dyes, trisazo dyes, xanthene dyes, proflavine dyes, sulfonaphthalein dyes, phthalocyanine dyes, carotenoid dyes, carminic acid dyes, azure dyes, acridine dyes, and so forth. One particularly suitable class of dyes includes anthraquinone compounds, which can be classified for identification by their Color Index (CI) number. For instance, some suitable anthraquinones that can be used in the present disclosure, as classified by their "C1" number, include Acid Black 48, Acid Blue 25 (D&C Green No. 5), Acid Blue 40, Acid Blue 41, Acid Blue 45, Acid Blue 129, Acid Green 25, Acid Green 27, Acid Green 41, Mordant Red 11(Alizarin), Mordant Black 13 (Alizarin Blue Black B), Mordant Red 3 (Alizarin Red S), Mordant Violet 5 (Alizarin Violet 3R), Natural Red 4 (Carminic Acid), Disperse Blue 1, Disperse Blue 3, Disperse Blue 14, Natural Red 16 (Purpurin), Natural Red 8, Reactive Blue 2, and so forth.

Prior to application, the colorant is typically dissolved or dispersed in a solvent to form the ink. Any solvent capable of dispersing or dissolving the components is suitable. The concentration of solvent in the ink formulation is generally high enough to allow easy application, handling, etc.

The ink can also include various other components as is well known in the art, such as colorant stabilizers, photoinitiators, binders, solvents, surfactants, humectants, biocides or biostats, electrolytic salts, pH adjusters, etc. Other additives can also be included to improve ink performance, such as a chelating agent to sequester metal ions that could become involved in chemical reactions over time, a corrosion inhibitor to help protect metal components of the printer or ink delivery system, a biocide or biostat to control unwanted bacterial, fungal, or yeast growth in the ink, and a surfactant to adjust the ink surface tension.

Once the ink substantially transparent to infrared radiation is introduced into or onto the desired component of the composite article, the component can be inspected as described herein for its position relative to other components of the composite article. In one example, ink substantially transparent to infrared radiation can be introduced into spunbond laminate side panels.

In one example infrared inspection system used for inspecting a side seam of an article, a camera is capable of detecting a wavelength of up to 1000 nanometers. The associated filter is capable of detecting a wavelength greater than 850 nanometers. Infrared light is produced at wavelengths between 850 and 1050 nanometers. As a result, inspection is performed with infrared radiation with a wavelength range of 850-1000 nanometers. For inks to be invisible or transparent to this inspection system, the inks must exhibit properties that fall outside of this wavelength range. Testing of inks with as little as one percent carbon black has shown that such inks can block infrared inspection. Although not limiting as an explanation, it appears that virtually any amount of carbon black colorant in an ink can impede infrared inspection, because it is hypothesized that the carbon black must be absorbing light within the range of 850-1000 nanometers used in the inspection system.

In practice, the inspection system of the present disclosure can be used to inspect a disposable absorbent article having multiple components. In this aspect, the article has an inspection region that is the region of inspection interest, particularly in the situation in which the inspection region includes a junction of two components. The inspection region is subject to inspection using infrared radiation. The inspection system of this aspect is especially useful with the presence of a printed graphic in the inspection region, and when the ink used to print the graphic includes no carbon black colorant such that the printed graphic is substantially transparent to infrared radiation. The junction can in one example be the area in which a side panel is affixed to an outer cover to form a seam. The printed graphic can cover the entire inspection region. As described above, the inspection region can also include an infrared blocker. Of particular interest are inks for which the ink has a CIELab L* less than 80 and a CIELab C* greater than 1.5, although the ink can have a CIELab L* less than 75 and a CIELab C* greater than 3, a CIELab L* less than 70 and a CIELab C* greater than 4.0, or any other suitable combination of a CIELab L* and CIELab C*.

In one aspect of the present disclosure, instead of simply introducing the ink substantially transparent to infrared radiation into only a single component of a composite product for registration of the single component, one or more of the same or different inks substantially transparent to infrared radiation can be introduced into more than one component for registration. In this aspect, the identical ink substantially transparent to infrared radiation can be introduced into or onto more than one component of a composite product to allow for the indication of registration for numerous components and the determination of the position of each component relative to other components of the composite product.

Greater detail with respect to infrared detection processes and equipment is provided in greater detail in U.S. Pat. No. 6,927,857 to Koele et al. as referenced above. From the above description, it should be apparent that the present disclosure can be used to determine, among other things, whether one or more components are properly positioned in a wide array of composite articles. While suited for a wide variety of applications, the present disclosure is particularly useful in the production of absorbent articles, such as disposable diapers, training pants, incontinence devices, sanitary napkins, and the like.

While an exemplary process for detecting a presence of a single component has been described above, it should be readily apparent that more than one and in fact many different components may be similarly detected, including components which include infrared markers for the purpose of providing or enhancing their infrared responses to incident radiation.

When introducing elements of the present disclosure or the preferred aspect(s) thereof, the articles "a", "an", "the", and "the" are intended to mean that there are one or more of the elements. The terms "comprising," "including", and "having" are intended to be inclusive and mean that there can be additional elements other than the listed elements.

The disclosure has been described with reference to various specific and illustrative aspects and techniques. However, it should be understood that many variations and modifications can be made while remaining within the spirit and scope of the disclosure. Many alternatives, modifications and variations will be apparent to those skilled in the art in light of the foregoing description. Accordingly, this disclosure is intended to embrace all such alternatives, modifications, and variations that fall within the spirit and scope of the appended claims.

We claim:

1. A method for manufacturing a disposable absorbent article including a printed graphic, the method comprising:
   printing an article component with ink free of carbon black, wherein the printed graphic has a CIELab L* less than 80 and a CIELab C* greater than 1.5;
   joining the article component to a second article at a junction to form the article, wherein the printing coincides with the junction; and
   passing the article through an infrared inspection station to inspect the junction without interference from the printing.

2. The method of claim 1, wherein the printed graphic has a CIELab L* less than 75 and a CIELab C* greater than 3.

3. A method for controlling the manufacture of a disposable absorbent article, the method comprising:
   printing first and second components with an ink transparent to infrared radiation;
   aligning the printed first component with the printed second component;
   affixing the first component to the second component to form a junction;
   passing the junction through an infrared inspection station to confirm the alignment of the first and second components.

4. A process for detecting whether one or more components are properly positioned in a composite article, the process comprising:
   printing one or more components of the composite article with an ink transparent to infrared radiation;
   irradiating the composite article with infrared radiation;
   producing an image from the near infrared or infrared radiation received from the irradiated composite article;
   identifying a position of a first variation in the produced image which represents an edge position of a first component in the composite article; and comparing the identified position with predetermined position data to thereby determine whether the first component is properly positioned in the composite article.

* * * * *